US010799551B2

(12) United States Patent
Kim et al.

(10) Patent No.: US 10,799,551 B2
(45) Date of Patent: Oct. 13, 2020

(54) COMPOSITION FOR ENHANCING COGNITIVE FUNCTION COMPRISING GREEN TEA EXTRACT WHICH HAS MODIFIED AMOUNTS OF INGREDIENTS

(71) Applicants: AMOREPACIFIC CORPORATION, Seoul (KR); INDUSTRY-ACADEMIC COOPERATION FOUNDATION, YONSEI UNIVERSITY, Seoul (KR)

(72) Inventors: Hyungsu Kim, Yongin-si (KR); Ayoung Kim, Yongin-si (KR); Juewon Kim, Yongin-si (KR); Si Young Cho, Yongin-si (KR); Yong-Deog Hong, Yongin-si (KR); Seung Soo Chung, Seoul (KR); Suk Jin Ko, Seoul (KR); Ji Hyun Jeong, Seoul (KR); Ji Woong Ahn, Seoul (KR)

(73) Assignees: AMOREPACIFIC CORPORATION, Seoul (KR); INDUSTRY-ACADEMIC COOPERATION FOUNDATION, YONSEI UNIVERSITY, Seoul (KR)

(*) Notice: Subject to any disclaimer, the term of this patent is extended or adjusted under 35 U.S.C. 154(b) by 168 days.

(21) Appl. No.: 16/110,299

(22) Filed: Aug. 23, 2018

(65) Prior Publication Data

US 2019/0091275 A1 Mar. 28, 2019

(30) Foreign Application Priority Data

Sep. 25, 2017 (KR) .................. 10-2017-0123106
Jun. 8, 2018 (KR) .................. 10-2018-0066159

(51) Int. Cl.
*A61K 36/82* (2006.01)
*A61P 25/00* (2006.01)
*A61K 31/353* (2006.01)

(52) U.S. Cl.
CPC ............ *A61K 36/82* (2013.01); *A61K 31/353* (2013.01); *A61P 25/00* (2018.01); *A61K 2236/33* (2013.01)

(58) Field of Classification Search
CPC ...................................................... A61K 36/82
See application file for complete search history.

(56) References Cited

U.S. PATENT DOCUMENTS

2002/0151506 A1 10/2002 Castillo et al.

FOREIGN PATENT DOCUMENTS

| JP | 200696740 A | 4/2006 |
|---|---|---|
| KR | 1020070015612 A | 2/2007 |
| KR | 1020100084165 A | 7/2010 |
| KR | 1020140077382 A | 6/2014 |
| WO | 2009057000 A2 | 5/2009 |
| WO | 2005113489 A1 | 12/2015 |

OTHER PUBLICATIONS

Korean Office Action dated Feb. 12, 2019, 16 pages.
Korean Notice of Allowance dated Jul. 29, 2019, issued in KR Application No. 10-2018-0066159.

*Primary Examiner* — Rosanne Kosson
(74) *Attorney, Agent, or Firm* — Cantor Colburn LLP

(57) ABSTRACT

Disclosed is to provide a composition derived from a natural material and which has an excellent effect of enhancing cognitive function and a method for preparing the same. The extract and composition according to one aspect of the present disclosure are derived from a natural material and thus are safe. It can prevent, ameliorate and treat cognitive decline. Therefore, it allows to improve the quality of life of the elderly population without concerns about side effects and promote development of the related industry.

15 Claims, 10 Drawing Sheets

COMPOSITION FOR ENHANCING COGNITIVE FUNCTION COMPRISING GREEN TEA EXTRACT WHICH HAS MODIFIED AMOUNTS OF INGREDIENTS

CROSS-REFERENCE TO RELATED APPLICATION

This application claims the priority of Korean Patent Application No. 10-2017-0123106, filed on Sep. 25, 2017 and Korean Patent Application No. 10-2018-0066159, filed on Jun. 8, 2018 and all the benefits accruing therefrom under 35 U.S.C. § 119, the contents of which in its entirety are herein incorporated by reference.

BACKGROUND

1. Field

The present disclosure relates to a composition for enhancing cognitive function comprising a green tea extract which has modified amounts of ingredients.

2. Description of the Related Art

Cognitive function is the ability to manipulate knowledge and information efficiently, including memory, spatial perception ability, judgment ability, executive function, and language ability. As we are becoming an aging society due to the development of medical technology and economic growth, physical damage caused by neurodegenerative diseases, which impair cognitive function and cognitive ability, and mental damage associated with the diseases are occurring.

Previously, cognitive decline often referred to a decline in the functions and abilities related to memory, etc. However, in recent years, it is considered that cognitive decline is not limited to memory decline but may cause the impairment of various abilities and regions, including complex attention, perception ability, executive function, learning ability, memory, language ability, perceptual-motor function, and social cognition, depending on the stage of change of the brain.

Dementia, which is a representative disease associated with cognitive decline, is a pathological condition that should be distinguished from normal aging. Dementia is categorized into Alzheimer's disease, vascular dementia, dementia caused by alcoholism, dementia caused by external injury, and dementia caused by Parkinson's disease according to the cause.

It has been reported that Alzheimer's disease is a chronic neurodegenerative disease involving memory loss, obscure consciousness, space-time confusion, and disorders of higher cerebral functions, such as thinking ability, arithmetic ability, judgment ability, and common sense. Alzheimer's dementia is known as the most common form of dementia occurring in the elderly population. There are cases of occurrences of Alzheimer's dementia at relatively young ages, and its incidence increases twice every 5 years in the age range of 65 to 85 years. The onset mechanism of Alzheimer's dementia is not clearly known, but a decrease of acetylcholine function in the central nervous system is the most common phenomenon. Thus, administration of acetylcholine precursors or drugs inhibiting degradation of acetylcholine to increase the concentration of acetylcholine in the brain has been used to treat Alzheimer's dementia. Therefore, acetylcholinesterase inhibitors have been used as therapeutic agents for Alzheimer's dementia, alone or in combination with conventional cholinesterase inhibitors. Examples of representative drugs include tacrine, donepezil, rivastigmine, and galantamine. All of these drugs, which are acetylcholinesterase inhibitors, merely delay the progression of the disease and is not significantly effective in direct treatment of the disease. Also, they have limited therapeutic range at the beginning of the disease. Thus, efforts have been made to develop a drug that treats the underlying cause of Alzheimer's dementia.

Vascular dementia is mostly caused by damage to the brain cells due to the lack of blood supply to various parts of the brain caused by cerebral arteriosclerosis. Although vascular dementia and Alzheimer's dementia are different in cause, they are the same in that they cause damage to memory and learning ability.

As the elderly population is increasing, there is an increasing need for treatment and prevention of aging, degenerative neurological diseases and brain diseases. As a result, studies have been conducted to prevent, treat, alleviate and ameliorate these diseases and aging. However, conventional materials have problems such as unclear effects and side effects. Therefore, it is necessary to develop a therapeutic agent for solving these problems derived from a natural material.

SUMMARY

An object of the present disclosure is to provide a composition derived from a natural material and which has an excellent effect of enhancing cognitive function without toxicity and a method for preparing the same.

In order to achieve the above object, one aspect of the present disclosure provides a composition for ameliorating cognitive decline comprising as an active ingredient a green tea extract comprising 5 to 25% by weight of (−)-gallocatechin gallate (GCG) and 7 to 15% by weight of (−)-epigallocatechin gallate (EGCG) based on the total weight of the composition.

In another aspect, the present disclosure provides a method for ameliorating cognitive decline, comprising administering a composition comprising as an active ingredient a green tea extract comprising 5 to 25% by weight of (−)-gallocatechin gallate (GCG) and 7 to 15% by weight of (−)-epigallocatechin gallate (EGCG) based on the total weight of the composition to a subject in need thereof.

In another aspect, the present disclosure provides a composition for preventing or treating neurodegenerative diseases comprising as an active ingredient a green tea extract comprising 5 to 25% by weight of (−)-gallocatechin gallate (GCG) and 7 to 15% by weight of (−)-epigallocatechin gallate (EGCG) based on the total weight of the composition.

In another aspect, the present disclosure provides a method for preventing or treating neurodegenerative diseases, comprising administering a composition comprising as an active ingredient a green tea extract comprising 5 to 25% by weight of (−)-gallocatechin gallate (GCG) and 7 to 15% by weight of (−)-epigallocatechin gallate (EGCG) based on the total weight of the composition to a subject in need thereof.

In another aspect, the present disclosure provides a method for preparing the composition, comprising the steps of: (1) adding ethanol to green tea and performing extraction at 50 to 70° C. for 30 minutes to 4 hours; (2) removing ethanol by filtration and decompression; and (3) adding water, stirring the mixture at 70 to 100° C. for 3 to 8 hours and then concentrating it under reduced pressure.

DETAILED DESCRIPTION

Figure 1:
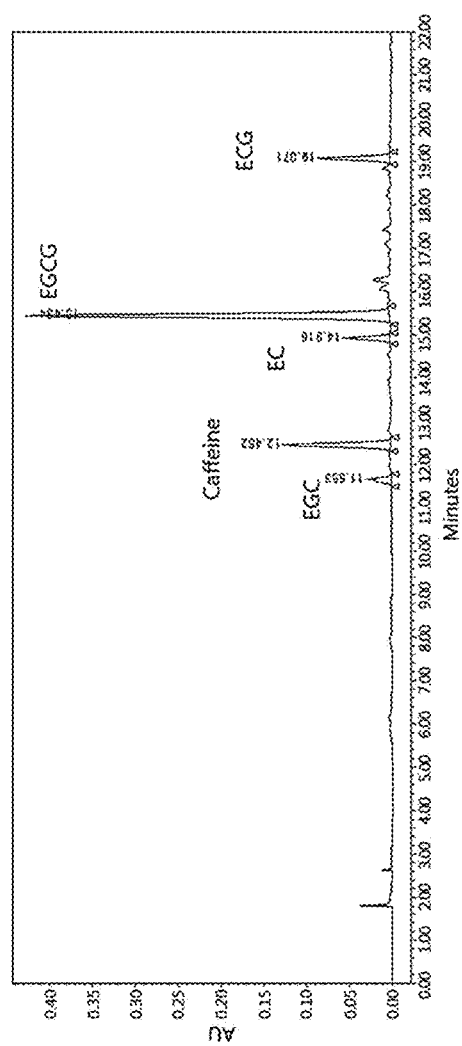
FIG. 1 is a chromatogram of the green tea extract notified by the Korean Ministry of Food and Drug Safety of Example 1 (Sample 1)

As used herein, the term "green tea extract" covers an extract of *Camellia sinensis*, an evergreen tree belonging to the family Theaceae, or an extract from tea leaves treated with *Bacillus subtilis* spp. and then fermented, etc., regardless of the extraction method, extraction solvent, and the form of the extracted ingredient or of the extract. It also covers fractions obtained by fractionating the extracts with a specific solvent. The tea includes at least one selected from the group consisting of tea leaves, flowers, stems, fruits, roots, and the cores of stems and roots. The tea may preferably be tea leaves. In addition, the extract may preferably be in powder form. The extraction or fractionation may be performed using water, an organic solvent, or a mixed solvent thereof. The organic solvent may be an alcohol, isopropanol, acetone, hexane, ethyl acetate, carbon dioxide, or a mixed solvent of two or more of them, although not limited thereto. The extraction or fractionation may be performed at room temperature or elevated temperature under conditions where the active ingredient of green tea is not destroyed or where the destruction is minimized. The alcohol may be a $C_1$ to $C_5$ lower alcohol. The number and method of the extraction or the fractionation is not particularly limited. For example, methods such as cold extraction, ultrasonic extraction, reflux cooling extraction, hot water extraction may be used. Preferably, the green tea extract of the present disclosure may be obtained by extracting or fractionating the active ingredient by cold or hot extraction, filtering the extract, and concentrating the filtrate under reduced pressure.

As used herein, the term "epicatechin" covers epigallocatechin (EGC), (−)epicatechin (EC), (−)-epigallocatechin gallate (EGCG), and epicatechin 3-O-gallate (ECG).

In one aspect, the present disclosure may relate to a composition for ameliorating cognitive decline comprising as an active ingredient a green tea extract comprising 5 to 25% by weight of (−)-gallocatechin gallate (GCG) and 7 to 15% by weight of (−)-epigallocatechin gallate (EGCG) based on the total weight of the composition or the extract.

In another aspect, the present disclosure provides a composition for preventing or treating neurodegenerative diseases comprising as an active ingredient a green tea extract comprising 5 to 25% by weight of (−)-gallocatechin gallate (GCG) and 7 to 15% by weight of (−)-epigallocatechin gallate (EGCG) based on the total weight of the composition.

In one aspect, the content of the GCG may be 5% by weight or more, 6% by weight or more, 7% by weight or more, 8% by weight or more, 9% by weight or more, 10% by weight or more, 11% by weight or more, 12% by weight or more, 12.52% by weight or more, 13% by weight or more, 14% by weight or more, 16% by weight or more, 18% by weight or more, 20% by weight or more, 22% by weight or more, or 24% by weight or more, based on the total weight of the composition or the extract. In another aspect, the content of the GCG may be 25% by weight or less, 23% by weight or less, 21% by weight or less, 19% by weight or less, 17% by weight or less, 15% by weight or less, 14% by weight or less, 13% by weight or less, 12.55% by weight or less, 12% by weight or less, 11% by weight or less, 10% by weight or less, 9% by weight or less, 8% by weight or less, 7% by weight or more, or 6% by weight or less, based on the total weight of the composition or the extract.

In one aspect, the content of the EGCG may be 7% by weight or more, 8% by weight or more, 8.48% by weight or more, 8.5% by weight or more, 9% by weight or more, 10% by weight or more, 12% by weight or more, or 14% by weight or more, based on the total weight of the composition or the extract. In another aspect, the content of the EGCG may be 15% by weight or less, 13% by weight or less, 11% by weight or less, 10% by weight or less, 9% by weight or less, 8.5% by weight or less, 8.48% by weight or less, 8.3% by weight or less, 8% by weight or less, or 7.5% by weight or less, based on the total weight of the composition or the extract.

In another embodiment, the total content of the GCG and the EGCG in the extract may be 40% by weight or less based on the total weight of the composition or the extract. In one aspect, the content of the catechin may be 40% by weight or less, 35% by weight or less, 30% by weight or less, 25% by weight or less, 20% by weight or less, 18% by weight or less, 16% by weight or less, 15% by weight or less, 14% by weight or less, 12% by weight or less, 10% by weight or less, 8% by weight or less, 6% by weight or less, or 4% by weight or less, based on the total weight of the composition or the extract. In another aspect, the total content of the GCG and the EGCG may be 3% by weight or more, 6% by weight or more, 8% by weight or more, 10% by weight or more, 12% by weight or more, 13% by weight or more, 14% by weight or more, 16% by weight or more, 18% by weight or more, 20% by weight or more, 25% by weight or more, 30% by weight or more, or 35% by weight or more, based on the total weight of the composition or the extract.

In another embodiment, the content of the epicatechin in the extract may be 20% by weight or less, based on the total weight of the composition or the extract. In one aspect, the content of the epicatechin may be 20% by weight or less, 18% by weight or less, 16% by weight or less, 15% by weight or less, 14% by weight or less, 12% by weight or less, 10% by weight or less, 8% by weight or less, 6% by weight or less, or 4% by weight or less, based on the total weight of the composition or the extract. In another aspect, the content of the catechin may be 3% by weight or more, 6% by weight or more, 8% by weight or more, 10% by weight or more, 12% by weight or more, 13% by weight or more, 14% by weight or more, 16% by weight or more, or 18% by weight or more, based on the total weight of the composition or the extract.

In another embodiment, the extract may be an extract obtained by at least one extraction with at least one selected from the group consisting of water and $C_1$ to $C_4$ alcohols. In one aspect, the alcohol may be ethanol. In another aspect, the alcohol may be at least 20%, at least 30%, at least 40%, at least 50%, at least 60%, or at least 70% ethanol. In another aspect, the alcohol may be up to 70%, up to 60%, up to 50%, up to 40%, or up to 30% ethanol.

In another embodiment, the content of the extract in the composition may be 1 to 100% by weight on a dry weight basis. In one aspect, the content of the extract in the composition may be 1% by weight or more, 10% by weight or more, 20% by weight or more, 30% by weight or more, 40% by weight or more, 50% by weight or more, 60% by weight or more, 70% by weight or more, 80% by weight or more, or 90% by weight or more on a dry weight basis. In another aspect, the content of the extract in the composition may be 100% by weight or less, 90% by weight or less, 80% by weight or less, 70% by weight or less, 60% by weight or less, 50% by weight or less, 40% by weight or less, 30% by weight or less, or 20% by weight or less on a dry weight basis.

In another embodiment, the dose of the active ingredient may be 5 mg/kg/day to 1000 mg/kg/day on a dry weight basis. In one aspect, the dose may be 5 mg/kg/or more, 100 mg/kg/or more, 200 mg/kg/or more, 300 mg/kg/or more, 400 mg/kg/or more, 500 mg/kg/or more, 600 mg/kg/or more, 700 mg/kg/or more, 800 mg/kg/or more, or 900 mg/kg/or more. In another aspect, the dose may be 1000 mg/kg/or less, 900 mg/kg/or less, 800 mg/kg/or less, 700 mg/kg/or less, 600 mg/kg/or less, 500 mg/kg/or less, 400 mg/kg/or less, 300 mg/kg/or less, 200 mg/kg/or less, 100 mg/kg/or less, 50 mg/kg/or less, or 10 mg/kg/or less.

In one embodiment, the cognitive decline may result from any one selected from the group consisting of neurotransmitter degradation, reduction of neurotransmitter production, and reduction of neurotransmitter receptors.

In another embodiment, the neurotransmitter may be acetylcholine.

Dementia is classified into Alzheimer's disease, vascular dementia, and other diseases according to the cause. Dementia patients generally show clinically significant impairment in intellectual ability, emotional and behavioral changes, etc. As the disease progresses, it results in severe cerebral cortical dysfunction such as loss of directional sensation, memory impairment, and aphasia. It is known that the pathological mechanism of Alzheimer's disease is as follows: First, the abnormal protein β-amyloid accumulates outside the neurons in the brain, and then the tau protein aggregates inside the neurons to damage the synapses, which ultimately leads to neurological dysfunction and brain cell death. In terms of neurobiochemistry, impairment of the cholinergic nervous system of the hippocampus and temporal lobe is particularly prominent in dementia. Impairment of these regions is directly or indirectly related to memory impairment. Biochemical dysfunction and neuron loss of the cholinergic nervous system of the basal forebrain pathway have been consistently reported by dementia researchers. In fact, it has been found that choline uptake and acetylcholine synthesis decrease in the hippocampus and cerebral cortex of dementia patients, and on the contrary, that acetylcholine esterase (AChE), which is an enzyme that degrades acetylcholine, is highly expressed in dementia patients. In addition, in dementia patients, the activity of choline acetyltransferase (ChAT), which is an enzyme that synthesizes acetylcholine, decreases sharply, and the reduction rate is the highest in the hippocampus. Also, the number of the nicotinic and/or muscarinic acetylcholine receptors (nAchRs and/or mAchRs) has been found to decrease in dementia patients. In one aspect, the present disclosure provides a composition for enhancing cognitive function using acetylcholine metabolism as the index. The composition according to one aspect of the present disclosure significantly enhances acetylcholine metabolism. Thus, it can significantly ameliorate cognitive decline, and further, considerably help to improve the quality of life, and ameliorate and treat the symptoms, of patients with cognitive decline, such as dementia patients, memory loss patients and amnesia patients.

In another embodiment, the cognitive decline may result from DNA methylation.

In another embodiment, the DNA methylation may result from DNA methyltransferase 1 (DNMT1). DNMT1 inhibits gene expression by causing DNA methylation, which leads to problems in BDNF expression, etc., resulting in cognitive decline. In one aspect, the present disclosure allows to inhibit the expression of DNA methyltransferase 1 (DNMT1) and thereby to inhibit DNA methylation, thus contributing to enhancement of cognitive ability.

In one embodiment, the cognitive decline may result from brain tissue lipid peroxidation.

In another embodiment, the cognitive decline may result from the peroxidation product malondialdehyde.

Lipid peroxidation refers to conversion of a lipid into a lipid peroxide. The fatty acid part of a lipid is peroxidized. Lipid peroxidation products include lipids having a hydroperoxyl group, lipids having an internally peroxidized structure, lipids having a hydroperoxyl radical, and in some cases, degradation products thereof. In general, the hydroperoxyl group is unstable and frequently generate radicals. It is believed that induction of a chain reaction of these radicals is a cause of tissue damage in organisms. In other words, lipofuscin, which appears in the nerves, liver, myocytes, etc. of aged animals, is thought to be an insoluble inhomogeneous polymer in which proteins, etc. are swept around lipid peroxides. Peroxidation of the membrane lipids changes the properties of the membrane such as permeability. Also, it is harmful to a living body as it is considered as a factor implicated in vascular lesion. Hydroperoxyl cholesterol is also known. Given its chemical structure, it can be considered as an alcohol peroxide. It is known to be clinically associated with aging. In particular, lipid peroxide is known to be a cause of brain aging. Thus, lipid peroxide leads to brain aging and cognitive decline. Therefore, it is possible to enhance cognitive function by reducing lipid peroxides. In one aspect, the present disclosure allows to decrease lipid peroxidation products in the brain tissues, thereby ameliorating brain aging and cognitive decline.

In another embodiment, the cognitive decline may be at least one selected from the group consisting of lethargy, memory deterioration, amnesia, cognitive deterioration, learning disability, attention decline, depression, hypoacusia, analgesia, anhydrosis, and discrimination decline.

In another embodiment, the cognitive decline may result from a neurodegenerative disease.

In one embodiment, the neurodegenerative disease is at least one selected from the group consisting of Alzheimer's disease, dementia, Parkinson's disease, Huntington's disease, autosomal-dominant cerebellar ataxia, narcolepsy, alcoholism, drug addiction and hereditary sensory and autonomic neuropathy.

In one embodiment, the composition may be a food or a pharmaceutical composition.

The formulation of the food composition is not particularly limited. However, the composition may be formulated into, for example, tablets, granules, pills, powders, liquids such as drinks, caramels, gels, bars, tea bags, etc. Each formulation may include an ingredient commonly used in the corresponding field in addition to the active ingredient. The ingredient may be selected and mixed by those skilled in the art without difficulty depending on the formulation or use and may provide a synergistic effect when applied with the other raw materials. Also, the food may be a health functional food.

The composition may be administered by various methods such as intake, drinking, injection, spraying or squeezing.

The determination of the dose of the active ingredient of the food composition according to one aspect of the present disclosure is within the knowledge of those skilled in the art. The dose may vary depending on various factors including the age, health condition, and complications of the subject.

The food composition according to one aspect of the present disclosure may be, for example, various foods such as chewing gums, caramel products, candies, frozen desserts, and confectionery, beverage products such as soft drinks, mineral water, and alcoholic beverages, and health functional foods including vitamins and minerals.

In addition to the above ingredients, the food composition according to one aspect of the present disclosure may comprise various nutrients, a vitamin, a mineral (electrolyte), flavoring agents such as a synthetic flavoring agent and a natural flavoring agent, a colorant and an improving agent (cheese, chocolate, etc.), pectic acid or a salt thereof, alginic acid or a salt thereof, an organic acid, a protective colloidal thickening agent, a pH adjuster, a stabilizer, a preservative, glycerin, an alcohol, a carbonating agent as used in carbonated beverages, etc. Besides, the food compositions according to one aspect of the present disclosure may comprise fruit flesh for the production of natural fruit juices, fruit beverages and vegetable beverages. These ingredients may be used alone or as a mixture thereof. The content of these additives is not so critical. However, generally it is 0 to about 60 parts by weight based on 100 parts by weight of the composition according to one aspect of the present disclosure.

The pharmaceutical composition according to one aspect of the present disclosure may be administered orally, parenterally, rectally, topically, transdermally, intravenously, intramuscularly, intraperitoneally, subcutaneously, etc. The formulation for oral administration may be a tablet, a pill, a hard or soft capsule, a granule, a powder, a fine granule, a liquid, an emulsion, or a pellet, although not limited thereto. The formulation for parenteral administration may be a solution, a suspension, an emulsion, a gel, an injection, a drop, a suppository, a patch, or a spray, although not limited thereto. The formulations can be easily prepared according to methods commonly employed in the art and may further comprise a surfactant, an excipient, a hydrating agent, an emulsifying accelerator, a suspending agent, a salt or buffer for controlling osmotic pressure, a colorant, flavoring, a stabilizer, a preservative, or other commonly used adjuvants.

The composition according to one aspect of the present disclosure may comprise a pharmaceutically acceptable salt, and the salt may comprise (1) an acid addition salt formed with an inorganic acid such as hydrochloric acid, hydrobromic acid, sulfuric acid, nitric acid, and phosphoric acid; or with an organic acid such as acetic acid, propionic acid, hexanoic acid, cyclopentane propionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2,2,2]-oct-2-en-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid, and muconic acid; or (2) a salt formed when an acidic proton present in the parent compound is substituted.

The dose of the pharmaceutical composition according to one aspect of the present disclosure will vary depending on the age, gender, body weight, pathological condition and severity of the subject, route of administration, and judgment of the prescriber. The determination of the dose of the active ingredient based on these factors is within the knowledge of those skilled in the art.

In another aspect, the present disclosure may relate to a method for preparing the composition, comprising the steps of: (1) adding ethanol to green tea and performing extraction at 50 to 70° C. for 30 minutes to 4 hours; (2) removing ethanol by filtration and decompression; and (3) adding water, stirring the mixture at 70 to 100° C. for 3 to 8 hours and then concentrating it under reduced pressure.

In one aspect, the ethanol may be at least 20%, at least 30%, at least 40%, at least 50%, at least 60%, or at least 70% ethanol. In another aspect, the ethanol may be up to 70%, up to 60%, up to 50%, up to 40%, or up to 30% ethanol.

In one aspect, the temperature of step (1) may be 50° C. or higher, 55° C. or higher, 60° C. or higher, 65° C. or higher, or 68° C. or higher. In another aspect, the temperature of step (1) may be 70° C. or lower, 65° C. or lower, 60° C. or lower, 55° C. or lower, or 52° C. or lower.

In one aspect, the time of step (1) may be 30 minutes or more, 40 minutes or more, 50 minutes or more, 60 minutes or more, 70 minutes or more, 80 minutes or more, 90 minutes or more, 100 minutes or more, 120 minutes or more, 140 minutes or more, 160 minutes or more, 180 minutes or more, 200 minutes or more, or 220 minutes or more. In another aspect, the time of step (1) may be 240 minutes or less, 220 minutes or less, 200 minutes or less, 180 minutes or less, 160 minutes or less, 140 minutes or less, 120 minutes or less, 100 minutes or less, 90 minutes or less, 80 minutes or less, 70 minutes or less, 60 minutes or less, 50 minutes or less, or 40 minutes or less.

In one aspect, the temperature of step (3) may be 70° C. or higher, 75° C. or higher, 80° C. or higher, 90° C. or higher, 95° C. or higher, or 98° C. or higher. In another aspect, the temperature of step (3) may be 100° C. or lower, 95° C. or lower, 90° C. or lower, 85° C. or lower, 80° C. or lower, or 75° C. or lower.

In one aspect, the stirring time of step (3) may be 30 minutes or more, 1 hour or more, 2 hours or more, 3 hours or more, 4 hours or more, 5 hours or more, 6 hours or more, or 7 hours or more. In another aspect, the stirring time of step (3) may be 8 hours or less, 7 hours or less, 6 hours or less, 5 hours or less, 4 hours or less, 3 hours or less, 2 hours or less, or 1 hour or less.

In another embodiment, the weight ratio of the product of step (2) and the water added in step (3) may be 1:7 to 1:12. In one aspect, the weight ratio may be 1:5 or more, 1:6 or more, 1:7 or more, 1:8 or more, 1:9 or more, 1:10 or more, 1:12 or more, 1:14 or more, 1:16 or more, or 1:18 or more. In another aspect, the weight ratio may be 1:20 or less, 1:18 or less, 1:16 or less, 1:14 or less, 1:12 or less, 1:11 or less, 1:10 or less, 1:9 or less, 1:8 or less, 1:7 or less, or 1:6 or less.

In another embodiment, the yield of the product after step (3) may be 5 to 30% by weight based on the weight of the green tea in step (1). In one aspect, the yield may be 5% by weight or more, 6% by weight or more, 8% by weight or more, 10% by weight or more, 12% by weight or more, 14% by weight or more, 16% by weight or more, 18% by weight or more, 20% by weight or more, 22% by weight or more, 24% by weight or more, 26% by weight or more, or 28% by weight or more. In another aspect, the yield may be 30% by weight or less, 28% by weight or less, 26% by weight or less, 24% by weight or less, 22% by weight or less, 20% by weight or less, 18% by weight or less, 16% by weight or less, 14% by weight or less, 12% by weight or less, 10% by weight or less, 8% by weight or more, or 6% by weight or less.

Hereinafter, the constitution and effects of the present disclosure will be described in more detail through examples, test examples, and formulation examples. However, the following examples are provided for illustrative purposes only to facilitate understanding of the present disclosure, and the scope of the present disclosure are not limited thereto.

Example 1: Preparation of a Green Tea Extract Notified by the Korean Ministry of Food and Drug Safety and a High Temperature Processed Green Tea Extract 1000 ml of 50% ethanol was added to 100 g of green tea (*Camellia sinensis*, O'sulloc Farm in Jeju) and the mixture was refluxed at 60° C. for 1 hour. The temperature of the sample was lowered to room temperature, followed by filtration. The filtrate was distilled under reduced pressure to obtain 23 g of a green tea extract notified by the Korean Ministry of Food and Drug Safety (GT-LE-35CAT, Sample 1) as a dark brown powder (yield: 23%).

10 g of Sample 1 was dissolved in 90 ml of water, and the mixture was stirred at 80° C. for 30 minutes to 8 hours. Then, the temperature was lowered to room temperature and the insoluble matter was filtered. The filtrate was concentrated under reduced pressure to obtain 10 g of a high temperature processed green tea extract. At this time, the contents of GCG, etc. of the high temperature processed green tea extract obtained at each of the stirring time intervals were measured using apparatuses as shown in Table 1 below, to identify changes in the contents of GCG, etc. over time (the contents of the ingredients in the extract at each time interval are as shown in Table 4) and identify the time zone in which GCG is most abundant. Stirring was stopped at the time zone and 10 g of a high temperature processed green tea extract (GT-LE-10GCG, HTP-GTE) was obtained. The thus-obtained extract was used as Sample 2.

Also, the contents of GCG, etc. of the high temperature processed green tea extract obtained at each of the stirring time intervals were measured using apparatuses as shown in Table 5 below, to identify changes in the contents of GCG, etc. over time (the contents of the ingredients in the extract at each time interval are as shown in Table 7). Stirring was stopped when the content of GCG reached 5 to 8% and 10 g of a high temperature processed green tea extract was obtained. The thus-obtained extract was used as Sample 3.

Figure 2:
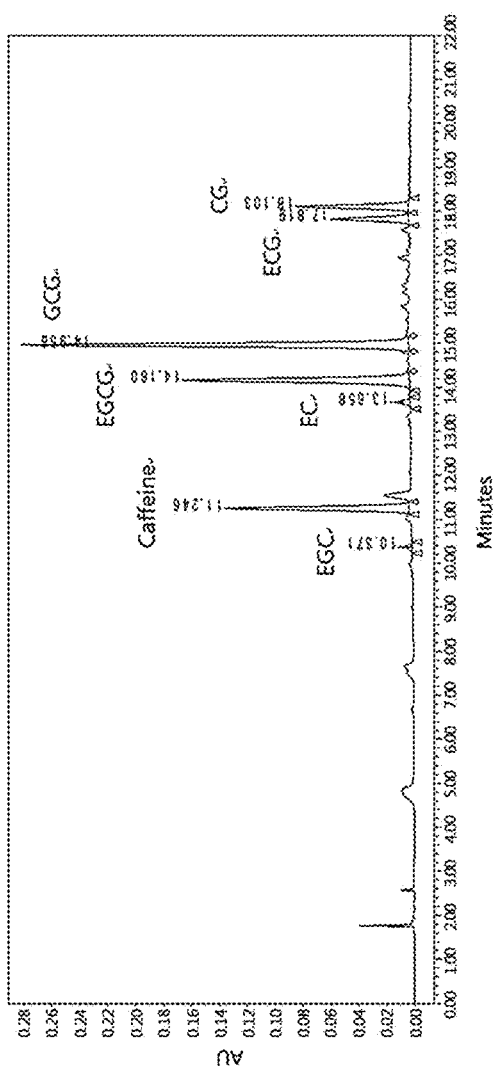
FIG. 2 is a chromatogram of a high temperature processed green tea extract according to one aspect of the present disclosure (Sample 2)

The conditions and results of the analysis of the composition of the three obtained extracts are shown in Table 1 to Table 3, Table 5 and Table 6, respectively. The chromatograms of two extracts are shown in FIG. 1 (Sample 1) and FIG. 2 (Sample 2). From the results, it was found that Sample 2 was different in composition from conventional green tea extract.

TABLE 1

| | Conditions of the analysis of composition |
|---|---|
| Column | Sun fire C18 5 um, 4.6 × 250 mm |
| Detector | UV 280 nm |
| Apparatus | Waters 2998 PDA Detector, Waters 1525 Pump, Waters 2707 Autosampler |
| Dilution | Gradient A: water with 0.1% TFA (trifluoroacetic acid), Gradient B: acetonitrile with 0.1% TFA |
| Gradient profile | 0 min A(95):B(5) 1 min A(95):B(5) 20 min A(71):B(29) 22 min A(71):B(29) |
| Flow rate | 1 ml/min |
| Injection volume | 20 μl |

TABLE 2

| Sample 1 | EGC | Caffeine | EC | EGCG | ECG | Total amount of epicatechin |
|---|---|---|---|---|---|---|
| | 9.16 | 3.21 | 3.63 | 20.93 | 2.62 | 36.34 |

TABLE 3

| Sample 2 | EGC | Caffeine | EC | EGCG | ECG | GCG | CG | Total amount of epicatechin | GCG + EGCG |
|---|---|---|---|---|---|---|---|---|---|
| | 2.16 | 3.28 | 0.75 | 8.48 | 1.90 | 12.52 | 2.38 | 13.28 | 21 |

TABLE 4

| Stirring time | EGCG | GCG | ECG | CG |
|---|---|---|---|---|
| 1 hour | 11.79 | 7.6 | 1.16 | 1.16 |
| 3 hours | 9.67 | 11.08 | 2.44 | 1.46 |
| 5 hours | 8.48 | 12.52 | 1.9 | 2.38 |
| 7 hours | 6.71 | 9.44 | 1.85 | 1.56 |

TABLE 5

| | Conditions of the analysis of composition |
|---|---|
| Column | Thermofisher C18 5 um, 4.6 × 250 mm |
| Detector | UV 280 nm |
| Dilution | Gradient A: water with 0.1% TFA (trifluoroacetic acid), Gradient B: acetonitrile with 0.1% TFA |
| Gradient profile | 0 min A(90):B(10) 30 min A(85):B(15) 42 min A(80):B(20) 44 min A(5):B(95) 49 min A(90):B(10) |
| Flow rate | 1 ml/min |
| Injection volume | 20 µl |

TABLE 6

| Sample 3 | EGC | Caffeine | EC | EGCG | ECG | GCG | CG | Total amount of epicatechin | GCG + EGCG |
|---|---|---|---|---|---|---|---|---|---|
| 4.56 | 4.58 | 2.27 | 2.27 | 2.27 | 2.79 | 7.59 | 0.87 | 20.01 | 17.98 |

TABLE 7

| Stirring time | EGCG | GCG | ECG | CG |
|---|---|---|---|---|
| 1 hour | 16.28 | 3.09 | 3.82 | 0.84 |
| 3 hours | 13.74 | 6.08 | 3.08 | 0.85 |
| 5 hours | 11.23 | 7.21 | 2.83 | 0.86 |
| 6 hours | 10.39 | 7.59 | 2.79 | 0.87 |

(In the above Table 2 to Table 4, Table 6 and Table 7, EGC denotes epigallocatechin, EC denotes (−)epicatechin, and ECG denotes epicatechin 3-O-gallate.)

(In the above Table 2 to Table 4, Table 6 and Table 7, the unit is % by weight based on the total weight of the sample.)

Test Example 1: Neurotoxicity Test

The PC12 cell line (neurocytoma) obtained from the Korean Cell Line Bank was seeded in a 96-well plate (FALCON) at $1\times10^5$ cells per well and cultured in a 5% $CO_2$ incubator at 37° C. for 24 hours. The cells were treated with 3, 10, 20, and 30 µg/ml of each of Sample 1 and Sample 2, and furthered cultured for 24 hours.

Then, the medium was removed, and then the cell viability was determined using Cell Counting Kit-8 (Dojindo). 10 µl of Cell Counting Kit-8 (Dojindo) solution was added to 100 µl of RPMI1640 (Lonza), and the mixture was applied to the cells. The number of living cells was quantified by measuring the absorbance at 450 nm. The cell count or cell viability (%) was calculated by the following equation:

Cell viability (%)=(absorbance of the sample-treated group−absorbance of the reaction reagent alone)/(absorbance of the untreated group−absorbance of the reaction reagent only)×100

Figure 3:
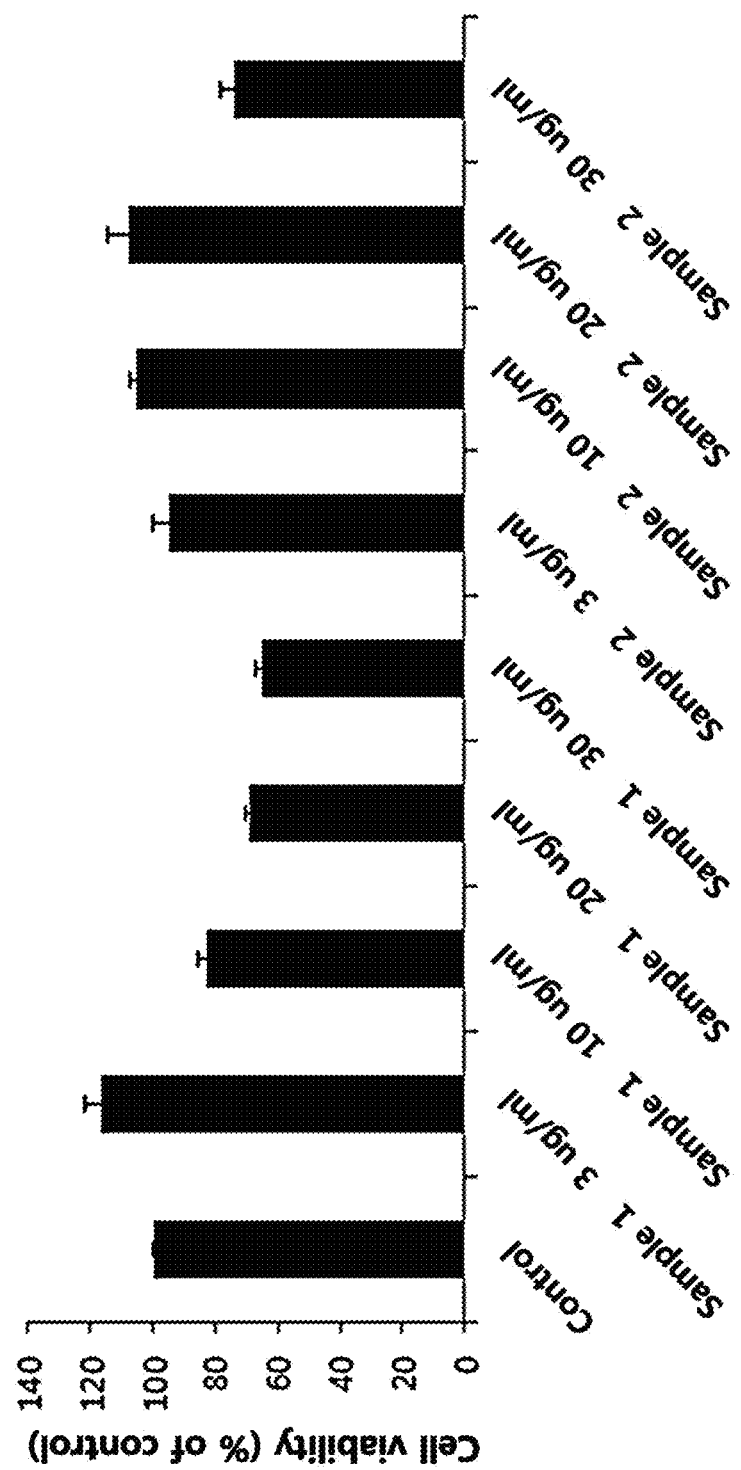
FIG. 3 shows the neurotoxicity test results of Sample 1 and Sample 2.

The results are shown in FIG. 3. From the results, it was found that Sample 2 was less cytotoxic to neurons than Sample 1.

Test Example 2: Acetylcholinesterase Activity Assay

Acetylcholine (ACh) is an organic molecule that acts as a neurotransmitter. It is involved in plasticity, arousal, reward, etc. and decreases in Alzheimer's patients. As acetylcholinesterase activity increases, acetylcholine decreases. Thus, it is possible to enhance cognitive function by inhibiting acetylcholinesterase activity.

The acetylcholinesterase inhibitory effect of each sample was identified using an acetylcholinesterase activity assay kit (Anaspec).

5 and 10 µg/ml of Sample 1 and Sample 2 were reacted with a reagent containing acetylcholinesterase for 1 hour. Then, the fluorescence intensity was measured at Ex/Em=490 nm/520 nm using a multiplate reader (Tecan). The acetylcholinesterase activity was determined by comparing the result with the fluorescence intensity of the untreated group. The equation for comparison of the activity is as follows:

Relative activity=(fluorescence intensity of the sample-treated group/fluorescence intensity of the untreated group)×100

Figure 4:
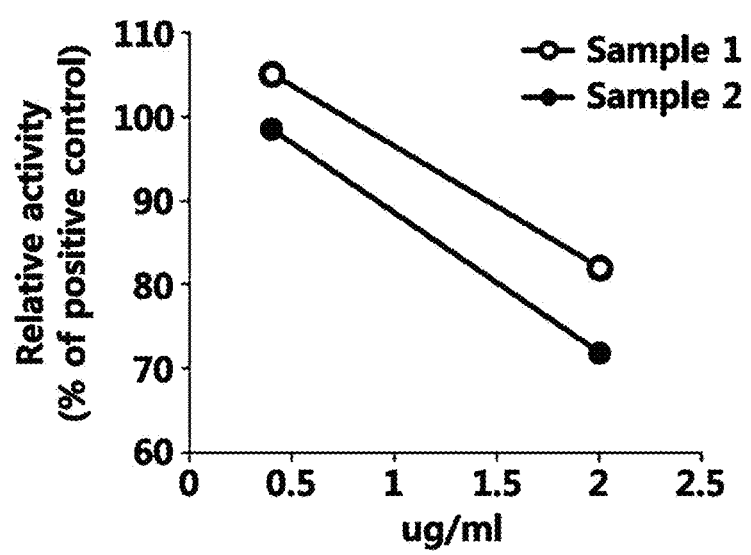
FIG. 4 shows the acetylcholinesterase activity assay results of Sample 1 and Sample 2.

The results are shown in FIG. 4. At the same concentration (2 µg/ml), Sample 2 showed higher acetylcholinesterase activity inhibitory effect than Sample 1. Also, 1.39 µg/ml of Sample 2 was needed to obtain the same acetylcholinesterase activity inhibitory effect as 2 µg/ml of Sample 1. Therefore, it was found that Sample 2 exhibited acetylcholinesterase activity inhibitory effect at a much smaller amount than Sample 1.

Test Example 3: DNMT1 (DNA (Cytosine-5)-Methyltransferase 1) Inhibition Assay The expression of the enzyme DNMT1 was measured using EpiQuik DNMT Activity/Inhibition Assay Ultra Kit (Epigentek).

Specifically, the enzyme DNMT1 was mixed with 10 µM and 50 µM of each of Sample 1 and Sample 2, followed by reaction at 37° C. for 90 minutes. The enzyme was then washed with a wash buffer provided in the kit, and a capture antibody recognizing methylated DNA was added, followed by incubation for 60 minutes. The enzyme was washed again with a wash buffer and then incubated with an antibody recognizing a capture antibody for 30 minutes. The enzyme was washed with a wash buffer once again. An enhancer solution was added thereto, followed by further incubation for 30 minutes. After being washed again, the enzyme was treated with a development solution for 10 minutes, and then the color change was observed. After 10 minutes, the reaction was terminated by adding a reaction termination solution. The absorbance was measured at 450 nm using a multiplate reader (Tecan). The percentage of inhibition of the absorbance of DNMT1 was calculated by comparing the result with that of the group not treated with a sample (enzyme alone).

Figure 5:
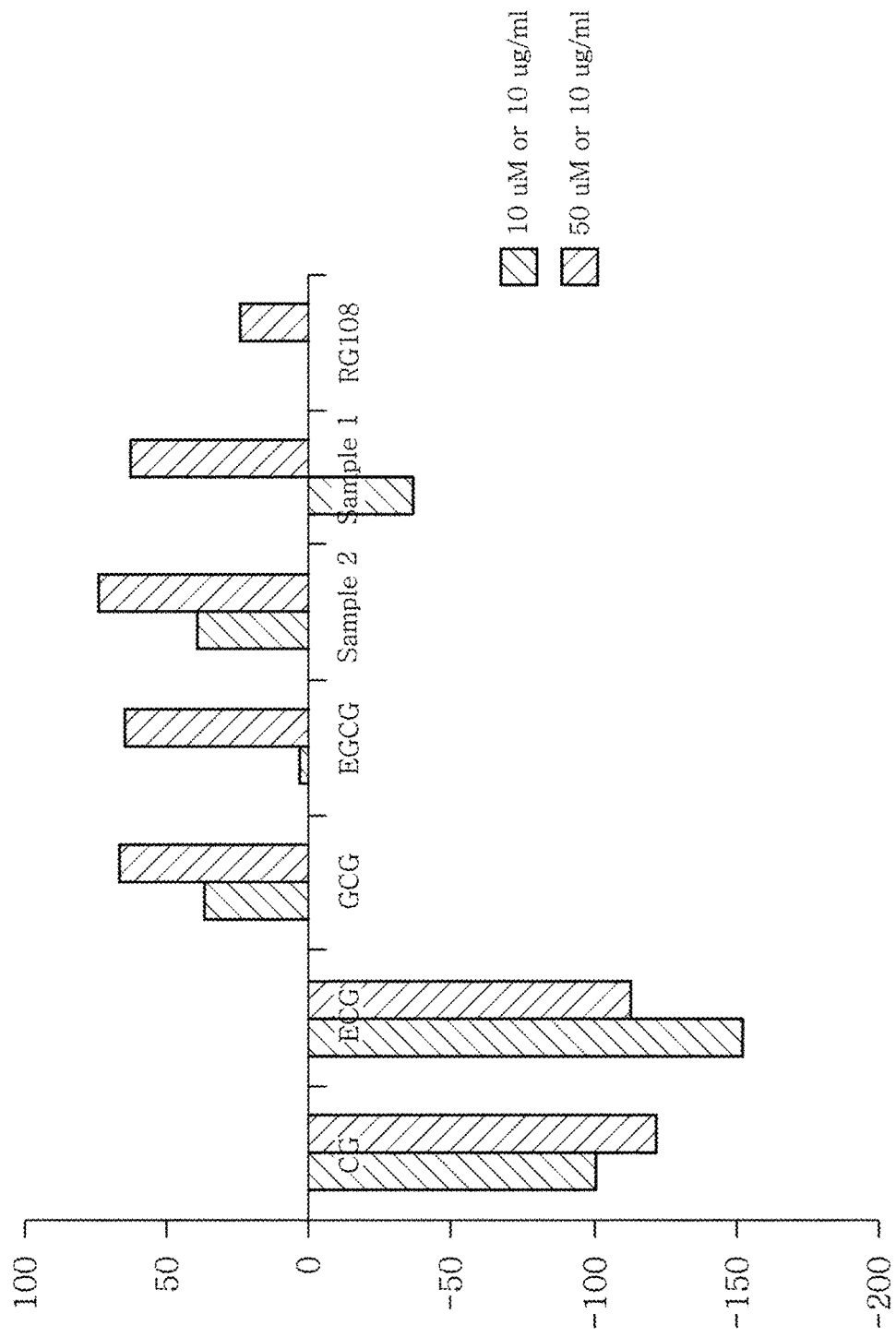
FIG. 5 shows the DNMT1 inhibition assay results of Sample 1 and Sample 2. "RG108" denotes the DNMT inhibitor N-phthaloyl-1-tryptophan.

From the results, it was found that Sample 2 had much higher DNMT1 expression inhibitory effect than Sample 1 at the same concentrations (10 and 50 µg/ml), as shown in FIG. 5. DNMT 1 (DNA methyltransferase 1) inhibits gene expression by inducing methylation of DNA. It is known that in a scopolamine-induced memory impairment model, BDNF (brain-derived neurotrophic factor) is methylated and acetylated, leading to suppression of its expression. Inhibition of DNMT 1 leads to an increase of the expression of BDNF in a scopolamine induced memory impairment model and thus results in enhancement of cognitive function. Thus, Sample 2 is much more effective in enhancing cognitive function than Sample 1.

Test Example 4: Lipid Peroxidation (MDA) Assay

In order to identify the antioxidative effect of each sample, the amount of lipid peroxide (malondialdehyde (MDA)) was measured using a lipid peroxidation (MDA) assay kit (SigmaAldrich).

Specifically, mice were orally administered with Sample 2 (100 mg/kg) or physiological saline for 4 weeks, and then administered with scopolamine (Sigma Aldrich) (3 mg/kg) or physiological saline for the last 6 days. At the last day, the brain was removed and homogenized in malondialdehyde (MDA) lysis buffer (Sigma Aldrich). The supernatant was then collected. 200 µl of the supernatant was reacted with 600 µl of TBA solution (Sigma Aldrich) at 95° C. for 1 hour, followed by cooling in an ice bath for 10 minutes. The absorbance was measured at 532 nm using a multiplate reader (Tecan). The amount of MDA was quantified by comparing the result with that of a reference sample, which was directly treated with malondialdehyde (MDA).

Figure 6:
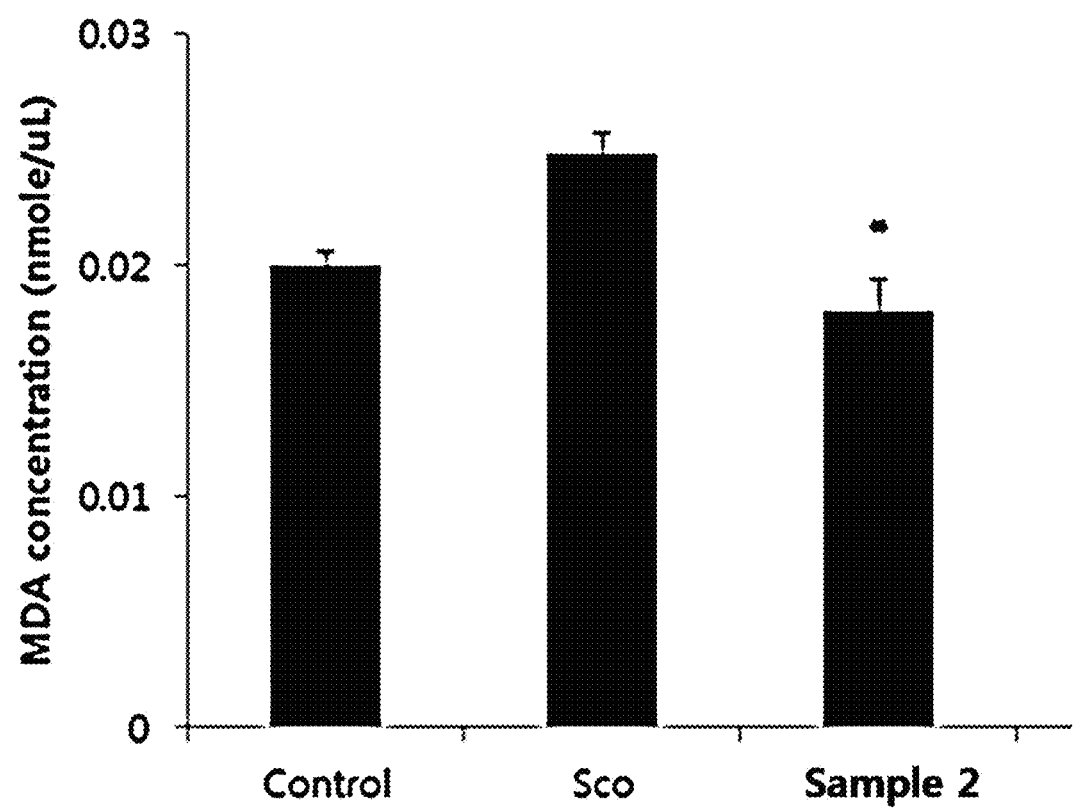
FIG. 6 shows the lipid peroxidation (MDA) assay results of Sample 2.

The results are shown in FIG. 6. From the results, it was found that the concentration of malondialdehyde (MDA) increased by the administration of scopolamine (Sco) was lowered by the intake of Sample 2 (100 mg/kg).

Test Example 5: Y-Maze Test

Y-maze test was performed to identify the ability of Sample 2 to protect cognitive ability, short-term memory, and spatial working memory.

Specifically, mice were orally administered with Sample 2 (100 mg/kg) or physiological saline for 4 weeks, and then administered with scopolamine (Sigma Aldrich) (3 mg/kg) or physiological saline for the last 6 days. One hour after the last dose, the mouse was placed on one arm of a Y-shaped maze (Jeung Do Bio & Plant Co., Ltd.) consisting of three arms (connected to each other at an angle of 120 degrees) and allowed to explore the maze freely. At this time, the movement of the mouse was recorded using a camera. Then, the number of entries into the other arms was checked to measure spontaneous alternation.

Spontaneous alternation (%)=(number of entries into the other arms/total number of arm entries−2 (number of the last choices))×100

Figure 7:
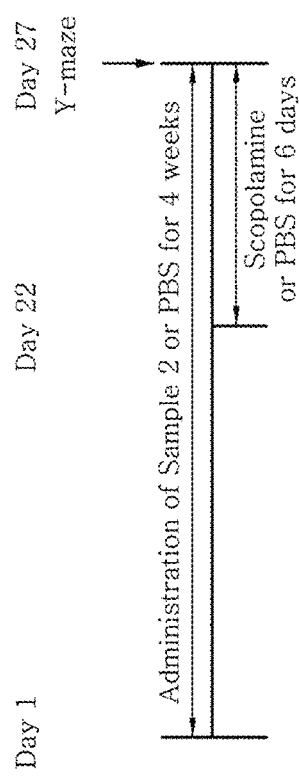
FIG. 7 shows the method and results of the Y maze test on mice administered with Sample 2.
Figure 7:
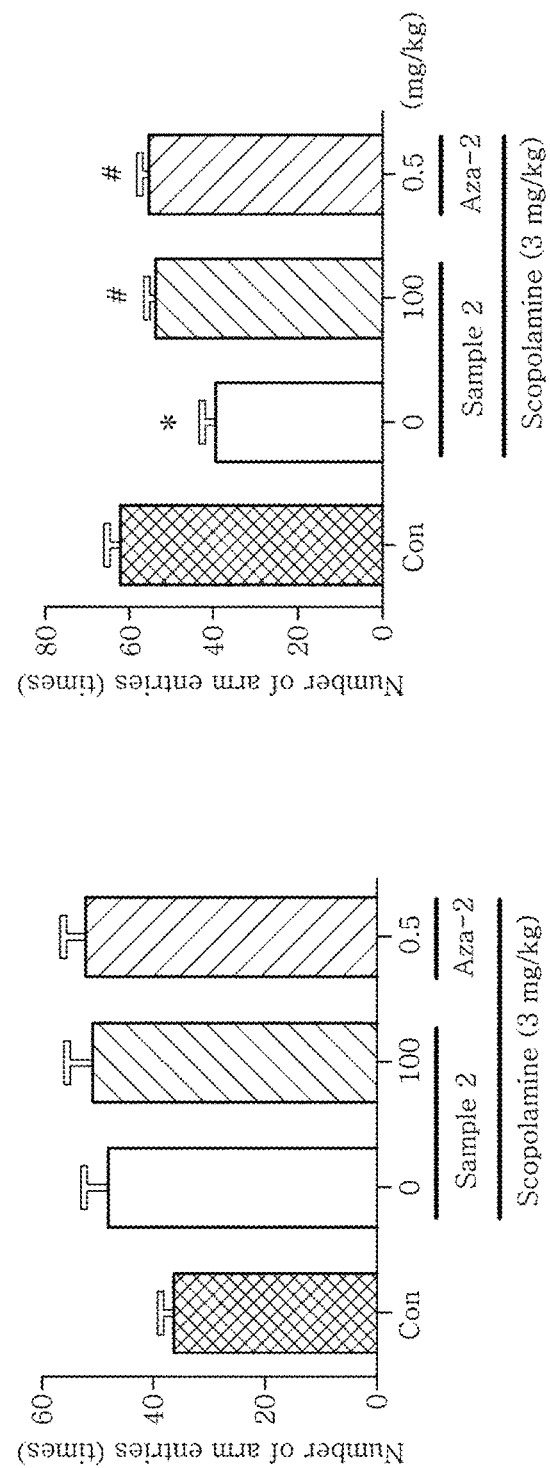

The results are shown in FIG. 7. From the results, it was found that the short-term memory damaged by the administration of scopolamine was recovered by the intake of Sample 2 (100 mg/kg), and that the effect was similar to that of Aza-2 (5-Aza-2'-deoxycytidine). Scopolamine acts on muscarinic receptors, on which the neurotransmitter acetylcholine (ACh) acts, to inhibit the neuronal activity induced by acetylcholine. Scopolamine increases the expression of DNMT1, which is a DNA methyltransferase, and thereby decreases the expression of BDNF, one of the neurotrophic factors, thus resulting in impaired memory. Thus, the intake of Sample 2 prevents and ameliorates the impairment of short-term memory by scopolamine.

Test Example 6: Amyloid Beta Aggregation Inhibition Assay

Amyloid beta is a protein commonly seen in Alzheimer's patients. It abnormally aggregates and accumulates outside neurons to form aggregates. The aggregated amyloid beta is toxic to neurons, causing synapse damage, neuron death, inflammation, mitochondrial damage, and oxidative stress and thus leading to Alzheimer's disease. In order to identify the ability of Sample 3 to inhibit amyloid beta aggregation, a measurement was made with an amyloid beta aggregation assay kit (Anaspec) using thioflavin T.

Figure 8:
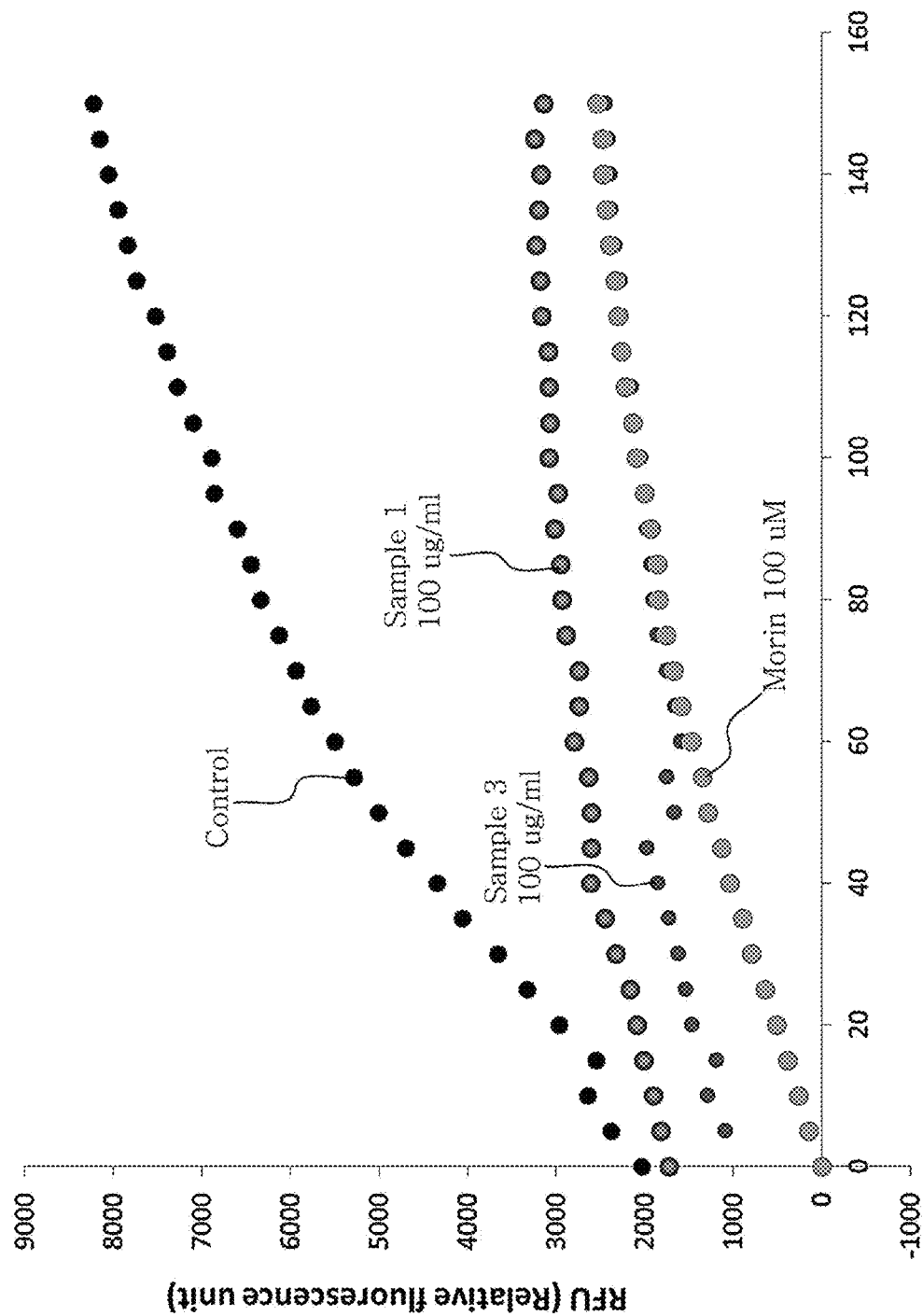
FIG. 8 shows the result of an assay of the ability of Sample 3 to inhibit amyloid beta aggregation.
Figure 9:
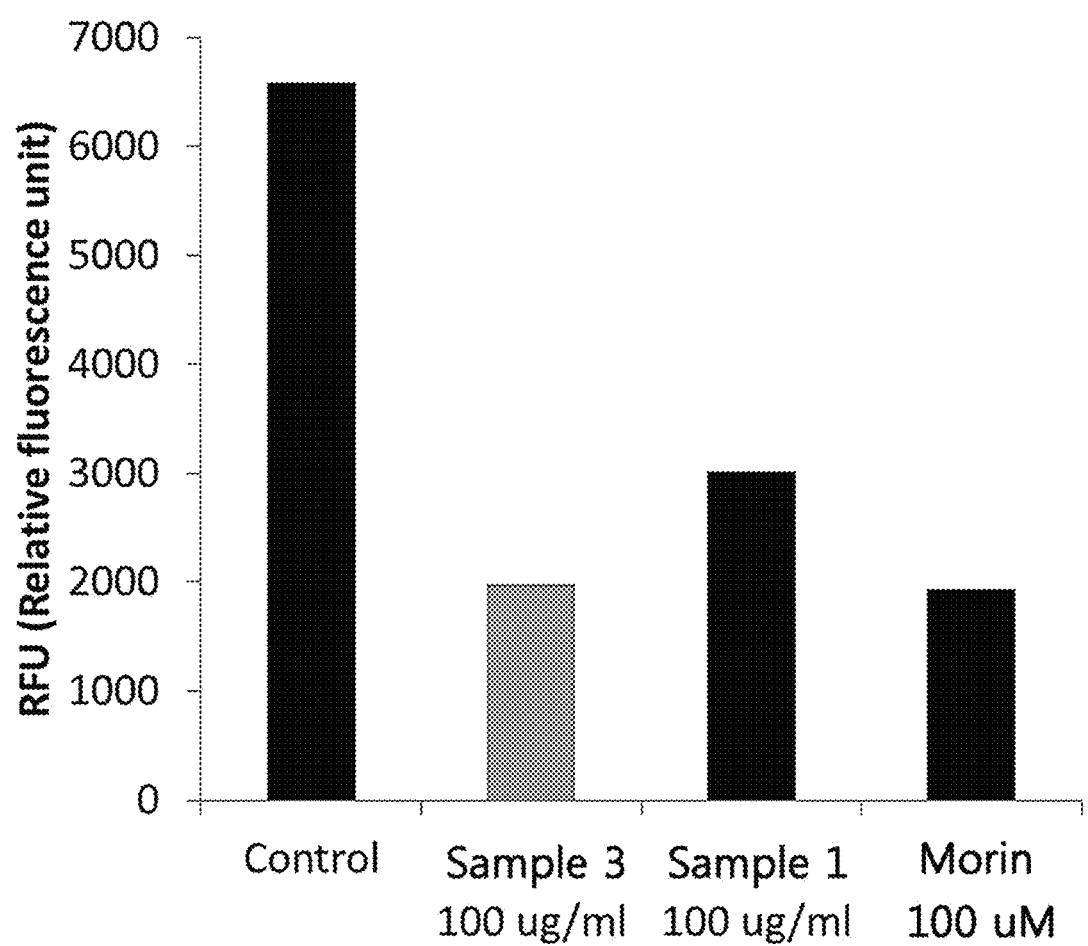
FIG. 9 shows the result of an assay of the ability of Sample 3 to inhibit amyloid beta aggregation.

Specifically, a thioflavin T solution was added to a 96-well plate (Falcon) to a final concentration of 20 µl, and then the sample was added to a final concentration of 100 µg/ml. Amyloid beta (1-42) was added thereto and the final volume was adjusted to 100 followed by incubation at 37° C. During the incubation, the fluorescence intensity was measured at Ex/Em=440 nm/484 nm every 5 minutes using a multiplate reader (Tecan). A test group treated with morin, which is one of the polyphenols known to have the effect of inhibiting amyloid beta aggregation, was used as the positive control group. The relative fluorescence intensity was calculated by the following equation:

Relative fluorescence unit=fluorescence intensity of the group treated with the sample amyloid beta−fluorescence intensity of the group treated with the sample alone The results are shown in FIG. 8 and FIG. 9. From the results, it was found that the amyloid beta aggregation over time was more effectively inhibited by Sample 3 than by Sample 1, and that the ability of Sample 3 to inhibit aggregation after a one-and-a-half-hour reaction was similar to that of morin of the positive control group.

Test Example 7: Determination of Protection Against Cell Death by Inhibition of Amyloid Beta Aggregation The SH-SY5Y cell line (neurocytoma) obtained from the Korean Cell Line Bank was seeded in a 96-well plate (FALCON) at $1\times10^4$ cells per well and cultured in a 5% $CO_2$ incubator at 37° C. for 24 hours. Amyloid beta (1-42, Abcam) was added to DMEM/F12 (Gibco) to a concentration of 40 µM. Each sample was added thereto to a concentration of 10 µg/ml. Then, they were allowed to react at 37° C. and 500 rpm for 24 hours using Thermomixer (Eppendorf) to induce aggregation. 24 hours after seeding, the medium was removed and the prepared amyloid beta aggregation-induced medium was added, followed by further culture for 24 hours.

After removing the medium, 100 µl of DMEM/F12 (Gibco) added with 20 µl of CellTiter 96 Aqueous One Solution Cell Proliferation Assay (Promega) was added to the cells. Then, the absorbance was measured at 490 nm to identify the number of living cells. The cell count or cell viability (%) was calculated by the following equation:

Cell viability (%)=(absorbance of the sample-treated group−absorbance of the reaction reagent only)/ (absorbance of the untreated group−absorbance of the reaction reagent only)×100

Figure 10:
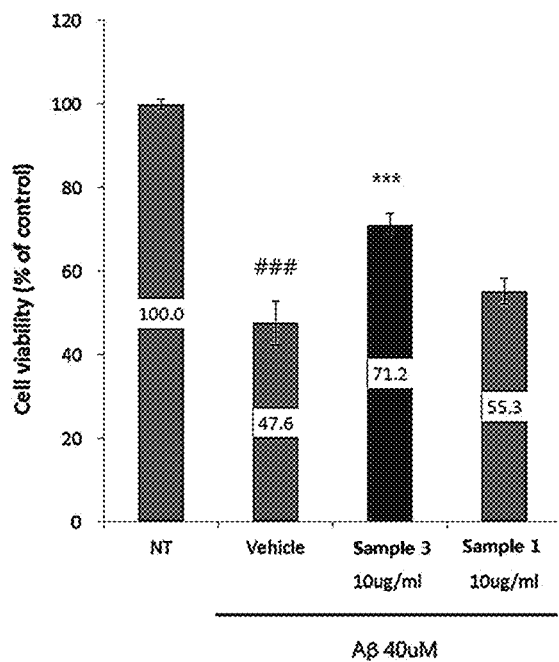
FIG. 10 shows the results of a test to determine protection against cell death by the inhibition of amyloid beta aggregation by Sample 3.

The results are shown in FIG. 10. From the results, it was found that Sample 3 inhibited amyloid beta aggregation compared to Sample 1 to prevent cell death caused by aggregated amyloid beta.

Test Example 8: Ex Vivo Measurement of Changes in Long-Term Potentiation (LTP)

Long-term potentiation (LTP) is an increase in transmission efficiency at the synapses of connected neurons. It is considered as a mechanism for the formation and storage of memory. In particular, the effect of promoting LTP induction in the hippocampus could lead to enhancement of the ability to form and store memory. Thus, a test for measuring LTP changes due to treatment with the samples of the present disclosure was performed. Specifically, the brains of 16-month-old male C57BL/6 mice were removed and placed in sucrose-artificial cerebrospinal fluid (CSF) (195.5 sucrose, 2.5 KCl, 1 NaH$_2$PO$_4$, 32.5 NaHCO$_3$, 11 Glucose, 2 Na pyruvate, 1 Na L-ascorbate, 5 MgSO$_4$, 0.5 CaCl$_2$)). Brain slices containing the Schaffer collateral pathway of the hippocampus (hippocampal pathway from CA3 to CA1) were prepared, transferred to artificial CFS (128.5 NaCl$_2$, 2.5 KCl, 1 NaH$_2$PO$_4$, 21.7 NaHCO$_3$, 11 Glucose, 2 Na pyruvate, 1 Na Lascorbate, 5 MgSO$_4$, 1 CaCl$_2$) at 35° C. and then allowed to react for 30 minutes to restore the tissue functions. The ion current was recorded by a typical field EPSP recording method using a patch clamp amplifier (Molecular Devices, USA). The measurement electrode was prepared with a borosilicate glass capillary (Sutter Instrument, USA). The electrode showing a resistance of 3 MΩ to 4 MΩ when filled with a solution was used for the test. A plate containing hippocampal slices was placed on an upright microscope and an extracellular fluid (124 NaCl, 2.5 KCl, 1 NaH$_2$PO$_4$, 26.2 NaHCO$_3$, 11 Glucose, 2 Na pyruvate, 1 Na Lascorbate, 3 MgSO$_4$, 1.5 CaCl$_2$)) was flowed through the plate at a flow rate of 1 to 2 ml/min by gravity. High frequency stimulation (HFS) (100 Hz, 500 ms, 4 times at 20-second intervals) was applied to the presynaptic axon fiber from CA3 treated and not treated with a sample to induce LTP of CA1 postsynapse. Then, the excitatory postsynaptic potential (EPSP) in the CA1 region was measured. The increase of excitatory postsynaptic potential was calculated by the following equation:

Increase of excitatory postsynaptic potential (%)=(potential after electrical stimulation)/(potential before electrical stimulation)×100

Figure 11:
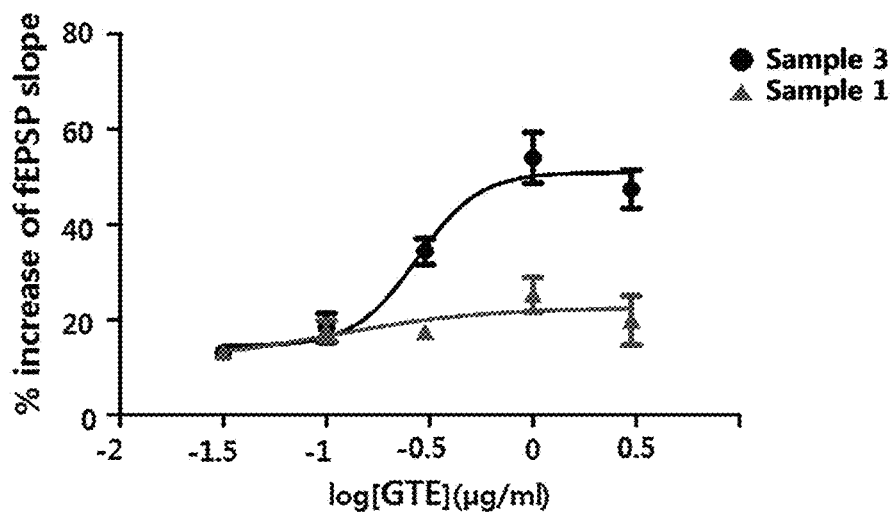
FIG. 11 shows the results of a test to identify the induction of long-term potentiation (LTP) by Sample 3.

The results are shown in FIG. 11. From the results, it was found that Sample 3 induced LTP more effectively than Sample 1 by further increasing the excitatory postsynaptic potential.

Formulation Example 1: Soft Capsule 150 mg of Sample 2 according to Example 1 was prepared and mixed with 440 mg of lactose, 430 mg of corn starch and 2 mg of magnesium stearate to prepare a soft capsule filling solution. Separately, a soft capsule sheet was prepared with 66 parts by weight of gelatin, 24 parts by weight of glycerin, and 10 parts by weight of sorbitol solution m and then filled with the filling solution to prepare a soft capsule.

Formulation Example 2: Tablet 150 mg of Sample 2 according to Example 1 was prepared and mixed with 15 mg of vitamin E, 15 mg of vitamin C, 250 mg of galactooligosaccharide, 60 mg of lactose, and 140 mg of maltose. The mixture was granulated using a fluidized bed dryer and then added with 8 mg of sugar ester. The resultant composition was tableted according to a conventional method to prepare a tablet.

Formulation Example 3: Drink 80 mg of Sample 2 according to Example 1 was prepared and mixed with 9 mg of vitamin E, 9 mg of vitamin C, 10 g of glucose, 0.6 g of citric acid, and 25 g of liquid oligosaccharide, followed by addition of 400 ml of purified water. The mixture was filled into a bottle and then sterilized at 30° C. for 4 to 5 seconds to prepare a drink.

Formulation Example 4: Granule 150 mg of Sample 2 according to Example 1 was prepared and mixed with 9 mg of vitamin E, 9 mg of vitamin C, 250 mg of anhydrous crystalline glucose, and 550 mg of starch. The mixture was granulated into granules using a fluidized bed granulator, which were then filled in a pouch to prepare granules.

Formulation Example 5: Health Food 150 mg of Sample 2 according to Example 1 was prepared and mixed with a mixture of vitamins (70 µg of vitamin A acetate, 1.0 mg of vitamin E, 0.13 mg of vitamin B1, 0.15 mg of vitamin B2, 0.5 mg of vitamin B6, 0.2 µg of vitamin B12, 10 mg of vitamin C, 10 µg of biotin, 1.7 mg of nicotinic acid amide, 50 µg of folic acid) and a mixture of inorganic substances (1.75 mg of ferrous sulfate, 0.82 mg of zinc oxide, 25.3 mg of magnesium carbonate, 15 mg of potassium phosphate monobasic, 55 mg of calcium phosphate dibasic, 90 mg of potassium citrate, 100 mg of calcium carbonate, 24.8 mg of magnesium chloride) to prepare a health food.

Formulation Example 6: Health Beverage 50 mg of Sample 2 according to Example 1 was prepared and mixed with 1000 mg of citric acid, 100 g of oligosaccharide, 2 g of plum concentrate, 1 g of taurine, and a balance of purified water to prepare 900 mL of a health beverage.

The extract and composition according to one aspect of the present disclosure are derived from a natural material and thus are safe. It can prevent, ameliorate and treat cognitive decline. Therefore, it allows to improve the quality of life of the elderly population without concerns about side effects and promote development of the related industry.

While the present disclosure has been described with respect to the specific embodiments, it will be apparent to those skilled in the art that the above is merely preferred embodiments and that the scope of the present disclosure is not limited thereto. Thus, the scope of the present disclosure is defined by the appended claims and their equivalents.

What is claimed is:

1. A method for ameliorating cognitive decline, comprising administering a therapeutically effective amount of a composition comprising as an active ingredient a green tea extract comprising 5 to 25% by weight of (−)-gallocatechin gallate (GCG) and 7 to 15% by weight of (−)-epigallocatechin gallate (EGCG) based on the total weight of the composition to a subject in need thereof.

2. The method according to claim 1, wherein the total content of the GCG and the EGCG in the extract is 40% by weight or less based on the total weight of the composition.

3. The method according to claim 1, wherein the extract is an extract obtained by at least one extraction with at least one solvent selected from the group consisting of water and Ci to C4 alcohols.

4. The method according to claim 1, wherein the content of the extract in the composition is 1 to 100% by weight on a dry weight basis.

5. The method according to claim 1, wherein the dose of the active ingredient is 5 mg/kg/day to 1000 mg/kg/day on a dry weight basis.

6. The method according to claim 1, wherein the cognitive decline results from any one selected from the group consisting of neurotransmitter degradation, reduction of neurotransmitter production, and reduction of neurotransmitter receptors.

7. The method according to claim 6, wherein the neurotransmitter is acetylcholine.

8. The method according to claim 1, wherein the cognitive decline results from DNA methylation.

9. The method according to claim 8, wherein the DNA methylation results from DNA methyltransferase 1 (DNMT1).

10. The method according to claim 1, wherein the cognitive decline results from brain tissue lipid peroxidation.

11. The method according to claim 10, wherein the cognitive decline results from the peroxidation product malondialdehyde.

12. The method according to claim 1, wherein the cognitive decline is at least one selected from the group consisting of lethargy, memory deterioration, amnesia, cognitive deterioration, learning disability, attention decline, depression, hypoacusia, analgesia, anhydrosis, and discrimination decline.

13. The method according to claim 1, wherein the cognitive decline results from a neurodegenerative disease.

14. The method according to claim 13, wherein the neurodegenerative disease is at least one selected from the group consisting of Alzheimer's disease, dementia, Parkinson's disease, Huntington's disease, autosomal-dominant cerebellar ataxia, narcolepsy, alcoholism, drug addiction and hereditary sensory and autonomic neuropathy.

15. The method according to claim 1, wherein the composition is a food or a pharmaceutical composition.

* * * * *